(12) United States Patent
Collazo

(10) Patent No.: US 7,867,234 B2
(45) Date of Patent: Jan. 11, 2011

(54) REAMER BUSHING

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1744 days.

(21) Appl. No.: 10/679,569

(22) Filed: Oct. 6, 2003

(65) Prior Publication Data
US 2005/0075638 A1 Apr. 7, 2005

(51) Int. Cl.
*A61B 17/32* (2006.01)
(52) U.S. Cl. .......................................... 606/80
(58) Field of Classification Search ............. 606/79–80, 606/86, 96; 623/20.34; 408/72 B, 97, 115 B, 408/115 R, 241 B
See application file for complete search history.

(56) References Cited

U.S. PATENT DOCUMENTS

| | | | |
|---|---|---|---|
| 3,981,604 A * | 9/1976 | Cenis ........................ | 408/72 B |
| 4,646,413 A * | 3/1987 | Nall et al. ................. | 29/402.03 |
| 5,100,408 A * | 3/1992 | Lackey ....................... | 606/79 |
| 5,514,140 A | 5/1996 | Lackey | |
| 5,534,005 A * | 7/1996 | Tokish et al. .................. | 606/80 |
| 5,613,970 A * | 3/1997 | Houston et al. ............... | 606/88 |
| 5,634,927 A * | 6/1997 | Houston et al. ............... | 606/96 |
| 5,709,689 A | 1/1998 | Ferrante et al. | |
| 5,735,856 A | 4/1998 | McCue et al. | |
| 5,810,829 A | 9/1998 | Elliott et al. | |
| 5,935,132 A | 8/1999 | Bettuchi et al. | |
| 6,063,091 A * | 5/2000 | Lombardo et al. ............ | 606/88 |
| 6,860,888 B2 * | 3/2005 | Ball et al. .................... | 606/104 |
| 2003/0163151 A1 * | 8/2003 | Ball et al. .................... | 606/167 |

* cited by examiner

*Primary Examiner*—Eduardo C Robert
*Assistant Examiner*—Tara R Carter
(74) *Attorney, Agent, or Firm*—Lerner, David, Littenberg, Krumholz & Mentlik, LLP

(57) ABSTRACT

A kit including tools or instruments for reaming a series of progressively larger bores in a work piece has as least two reamers of different reamers. Each of the reamers has a plurality of cutting flutes extending radially from a central shaft of the reamer. The flutes of each of the at least two reamers extend at a different radial distance from the shaft with the inner shaft of each reamer having the same diameter. A rotatable guide bushing has a recess for receiving each of the flutes of the at least two reamers with the recesses open to a central bore in the bushing. The central bore has a diameter equal to or greater than the shaft diameters of the reamers and acts as a guide to keep the rotational axis of each reamer aligned with the central axis of the bushing bore. A holder is provided to fix the bushing with respect to the bore in the work piece.

11 Claims, 15 Drawing Sheets

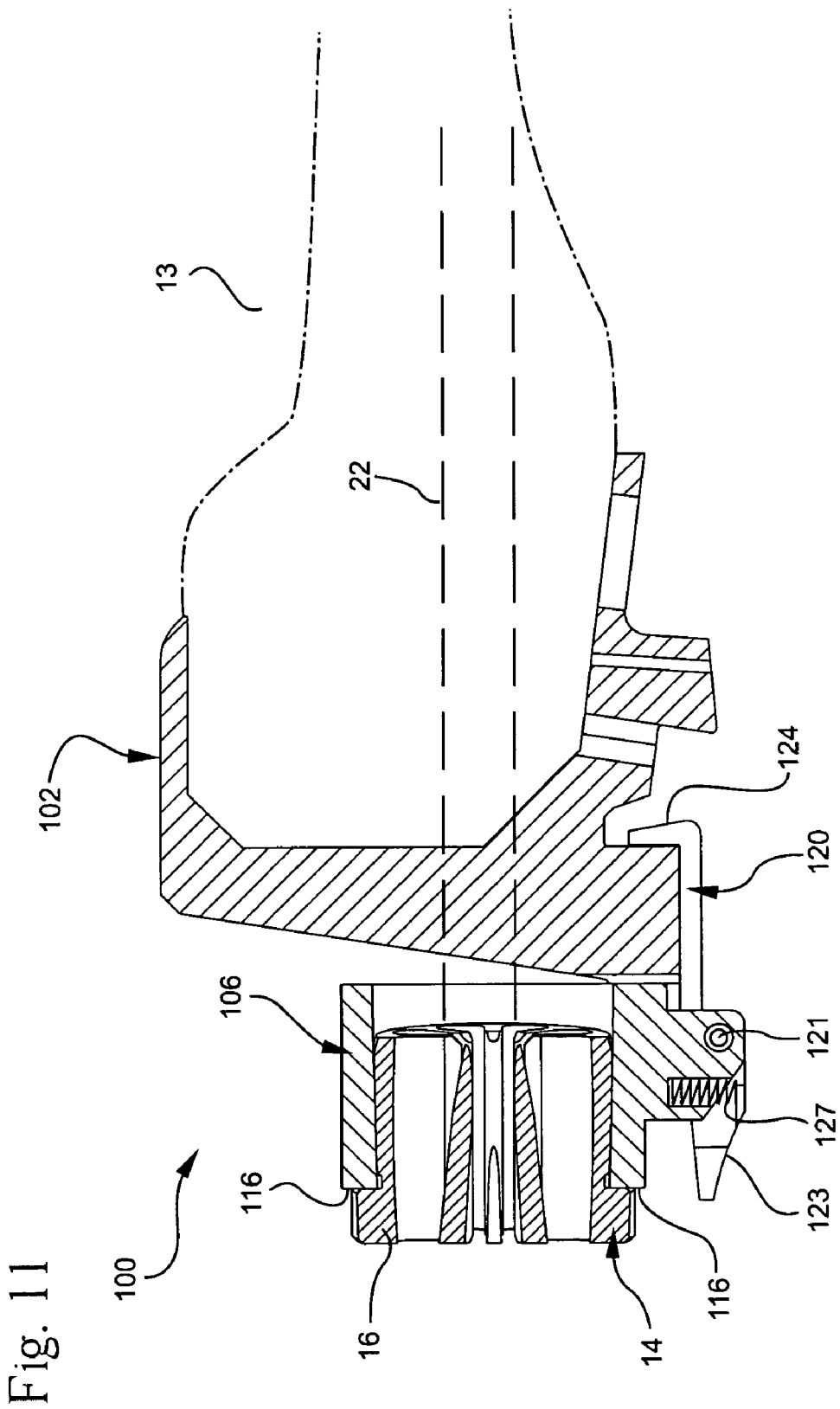

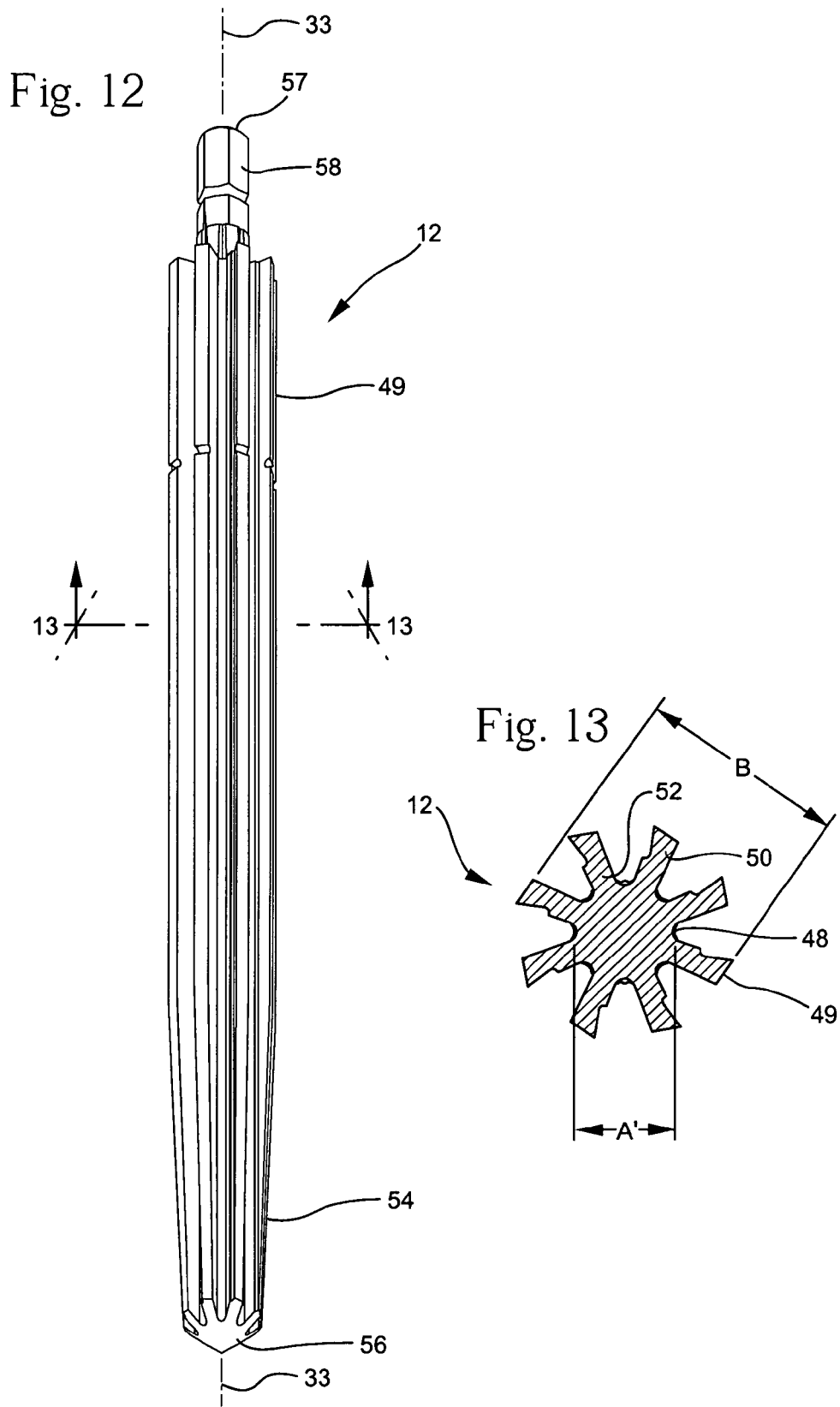

REAMER BUSHING

BACKGROUND OF THE INVENTION

The invention relates to a reaming system for progressively enlarging a bore. More particularly, it relates to a surgical reaming system for progressively enlarging a bone canal during orthopedic surgery.

Progressive reaming of bone canals is well known and discussed, for example, in U.S. Pat. Nos. 5,108,408 and 5,514,140. Progressive reaming systems can be used in the tibia or femur during knee replacement surgery, hip replacement surgery or for fracture fixation using nails. The systems utilize a plurality of reamers, each having different cutting diameters to prepare a bore for the stem of a knee prosthesis, femoral component or fracture fixation nail, for example. During such surgery, the surgeon initiates a reaming of the intramedullary canal using a smallest cutting diameter reamer selected from a set of reamers, and progresses up in selected incremental cutting diameters of the reamers until the desired size bore in the bone canal is achieved.

SUMMARY OF THE INVENTION

The present invention provides an instrumentation system for long bone surgery or in any application in which it is desired to enlarge a bore in a progressive manner. The present invention provides two or more reamers of different diameter in a set, a single rotatable bushing engageable with each of the reamers of the set and a bushing holder for holding the rotatable bushing in fixed alignment with respect to the bore to be reamed and enlarged.

It is a further object of the invention to provides a rotatable bushing which can accommodate a series of reamers each having flutes of a different diameter to create different size bores.

These and other objects of the invention are achieved by a kit of tools or instruments for reaming a series of progressively larger bores, which kit has at least two reamers. Each of the reamers has a plurality of flutes extending radially from a central shaft, the flutes of each reamer extend at different radial distances increasing from a smallest diameter reamer to a largest diameter reamer. However, the inner shafts of each reamer from which the flutes extend have the same diameter. This allows the use of a single rotatable guide bushing having a series of recesses for receiving each of the flutes of the reamers. The number of recesses in the bushing is equal to or greater than the number of flutes on the reamers. The recesses in the guide bushing are open to and extend radially outwardly from a central bore or opening, which central bore has a diameter equal to the constant inner shaft diameter of the reamers. The recesses extend radially from the central bore or opening a distance greater than or equal to the largest radial extent of the flutes of the largest reamer. Thus, each reamer from the smallest to the largest may be inserted within the rotatable bushing and be guided by the engagement between the inner shaft and central bore of the bushing to maintain coaxial alignment with the bore.

A holder is provided which can be fixed with respect to the bore to be enlarged, such as to the canal of a long bone. The rotatable guide bushing rotates on the fixed holder. It can be seen that the rotation of the rotatable bushing is caused by the rotation of the reamer, specifically the rotation of flutes acting against the recesses in the reamer bushing. The reamer, itself, has a drive end which may be driven by any convenient rotary power source such as a pneumatic or electric power drill.

As long as the bushing has a sufficient number of recesses to accommodate the reamer with the largest number of flutes, then reamers with fewer flutes may also be utilized. Of course, the flutes of the reamer must be angularly oriented about the circumference of the reamer at the same angle as the recesses in the bushing. Preferably, the reamer has eight flutes oriented at 45° increments around the circumference of the central shaft. Thus, the preferred bushing would have eight recesses oriented at 45° increments around the central bore. Obviously, more or fewer flutes can be used as long as the angular spacing of the recesses in the rotatable bushing corresponds to the angular orientation of the flutes. It can be seen that the preferred rotatable bushing is designed to accommodate eight flutes spaced at 45°. However, it could also accommodate a reamer having four flutes spaced at 90°. If the reamer has more than eight flutes, such as, for example, ten flutes, then the spacing of the recesses and the flutes would be at 36° increments around the circumference of the central reamer shaft/central bushing bore.

Furthermore, the reamer bushing could have at least three recesses for receiving one or more of the reamer flutes. Each recess may receive one, two or even three flutes. In addition, the flutes and reamer bushing recesses may be helically shaped as long as the root diameters of the reamer flutes conforms to the inner bore of the reamer.

While the instrumentation is designed for use primarily in enlarging bone canals such as in the femur and tibia, it can be seen that such instrumentation or tools can be used to enlarge a bore in any application where it is difficult to drill or ream a bore of a desired diameter in a single step. This may be where the work material is very hard and the stresses and/or heat produced on the tooling or work piece would be too high if a single large bore were drilled or reamed in a single step. Thus, one could drill a pilot hole in a work piece and then enlarge the pilot hole by use of the progressive reaming system or kit of the present invention in which a plurality of increasingly larger reamers are utilized to increase the size of the bore incrementally. When used in a bone canal, the diameter of the reamers progressively increases in 0.5, 1 or 2 mm increments. However, when utilized in other materials and in other diameters, the reamer diameters may be incrementally increased in any convenient amount, depending upon load and heat generation limitations.

BRIEF DESCRIPTION OF THE DRAWINGS

In order to facilitate insertion of the reamer into the preformed bore in the work piece during enlargement, the reamer tip may be tapered, such as conically tapered, in a manner well know in the art.

The invention can be performed in various ways and some embodiments will now be described by way of example and with reference to the accompanying drawings in which:

FIG. 11 is a cross-sectional view of the assembly shown in FIG. 9 along lines 11-11;

FIG. 12 is an isometric view of a pair of reamers of different diameter provided as part of a kit including the system of FIG. 1;

FIG. 13 is a typical cross-sectional view of one of the reamers of FIG. 12 along lines 13-13;

DETAILED DESCRIPTION

Figure 14:
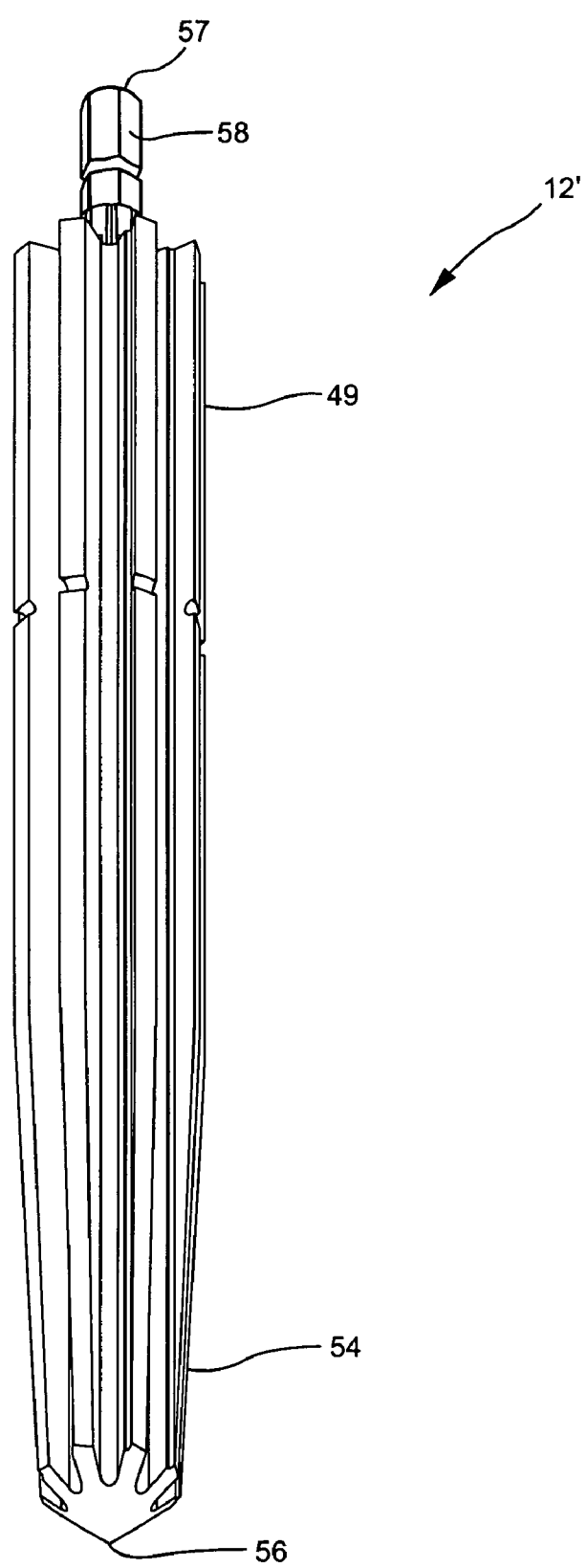
FIG. 14 is an elevation view of a second larger reamer which forms part of a kit of reamers and is usable with the reamer bushing of the present invention.
Figure 15:
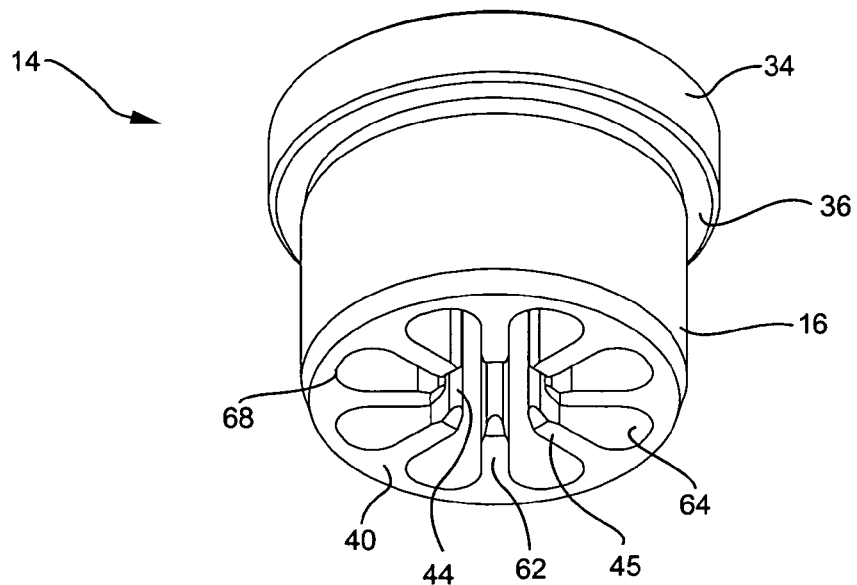
FIG. 15 is an isometric view of the reamer bushing of the present invention.
Figure 16:
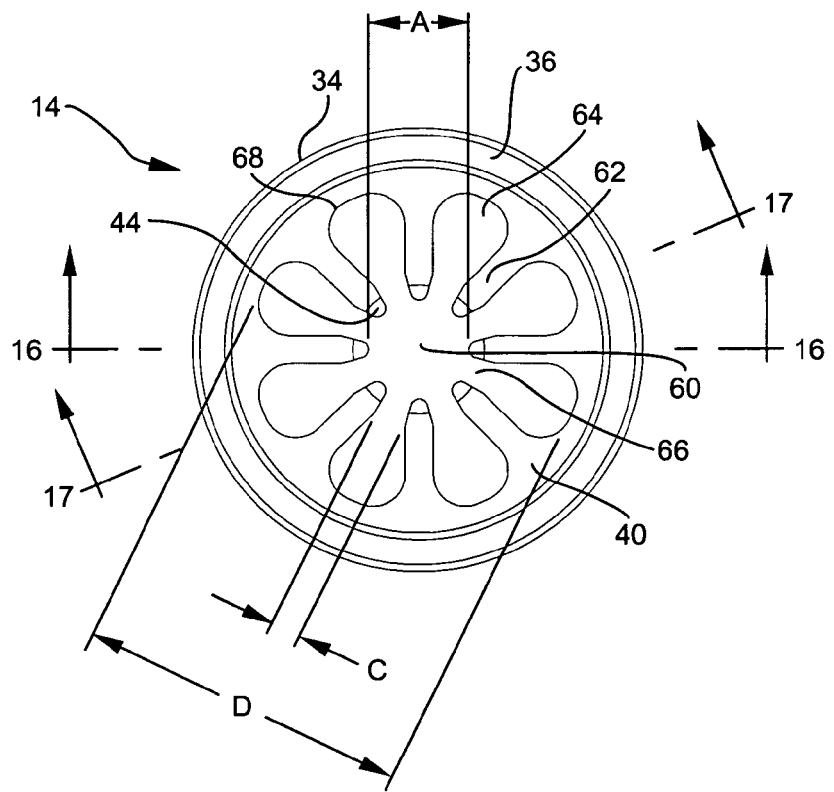
FIG. 16 is a bottom view of the reamer bushing shown in FIG. 15.
Figure 17:
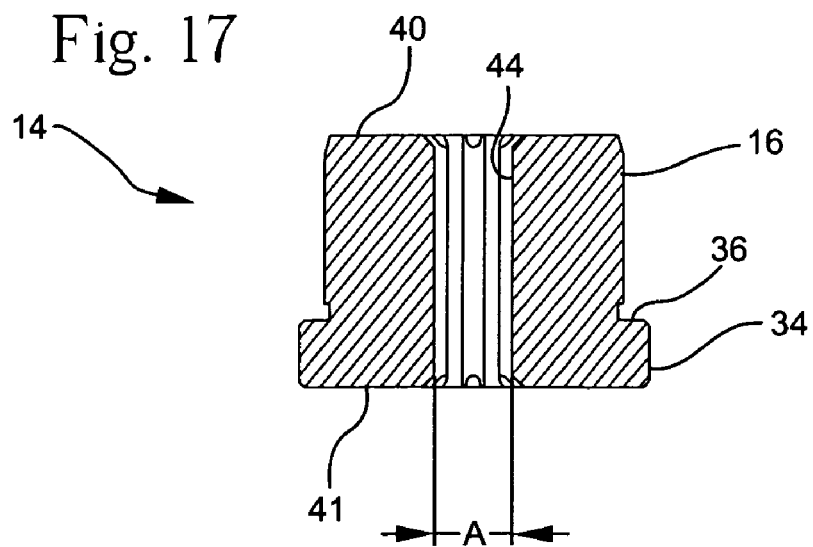
FIG. 17 is a cross-sectional view of the reamer bushing of FIG. 16 along lines 16-16.
Figure 18:
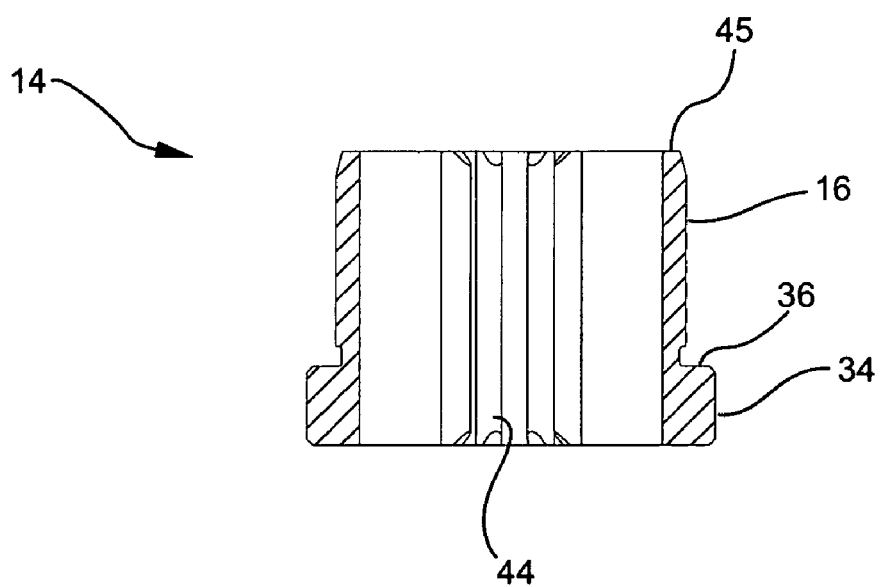
FIG. 18 is a cross-sectional view of the reamer bushing of FIG. 16 along lines 17-17.

Referring to FIGS. 1 through 4 and 12, there is shown a tibial reaming system or kit generally denoted as 10 comprising a series of reamers 12 and a reamer bushing 14 mounted in a bushing holder 18 attached over a long bone such as a tibia 11, for example, to a tibial mounting fixture such as trial baseplate 19. While two reamers 12, 12' of different diameter are shown in FIGS. 12 and 14, the kit may contain any desired number of reamers of different diameters. In the preferred embodiment, holder 18 has an inner guide bore 32 and a handle portion 20 for ease of use. Holder 18 preferably is removably attached to the proximal surface 21 of trial baseplate 19 in any convenient manner. Reamer bushing 14 has a bearing surface 16 adapted for rotation on an inner cylindrical bearing surface of guide bore 32 within bushing holder 18. Holder 18 is adapted to be mounted on trial 19 to locate bore 32 in a fixed position with respect to a bone canal bore 22. In the preferred embodiment, when bushing 14 is used in connection with tibia 11 and trial baseplate 19 in reaming the tibial canal, baseplate 19 is attached to the bone, for example, by being pinned to the proximal end of tibia 11 via a pair of pins 28 shown in FIG. 4.

In the preferred embodiment, to mount holder 18 on tibial baseplate 19, holder 18 includes a pair of tabs 30 which can be inserted into and lockingly engage recesses 24 in trial 19. In addition, holder 18 may include a locking pin 25 mounted with handle 20 to selectively engage a central portion 27 on the anterior of trial baseplate 19. Other mounting systems, such as screws, may be used as long as the mounting system ensures that holder 18 is fixed in position with respect to the long bone bore 22 during reaming.

In the preferred embodiment, mating bearing surfaces 16 and 32 of bushing 14 and holder 18 have a machined finish allowing rotation therebetween with low friction. The preferred bushing 14 also includes a flange 34 having an underside with a bearing surface 36 which engages a top surface 38 of bushing holder 18 (see FIG. 2). In the preferred embodiment, the depth of bore 32 and the height of bearing surface 16 are sized such that a bottom surface 40 of bushing 14 does not engage the upwardly or proximally facing surface 21 of trial 19. This reduces friction since bottom surface 40 of bushing 18 has a greater surface area than bearing surface 36.

Figure 1:
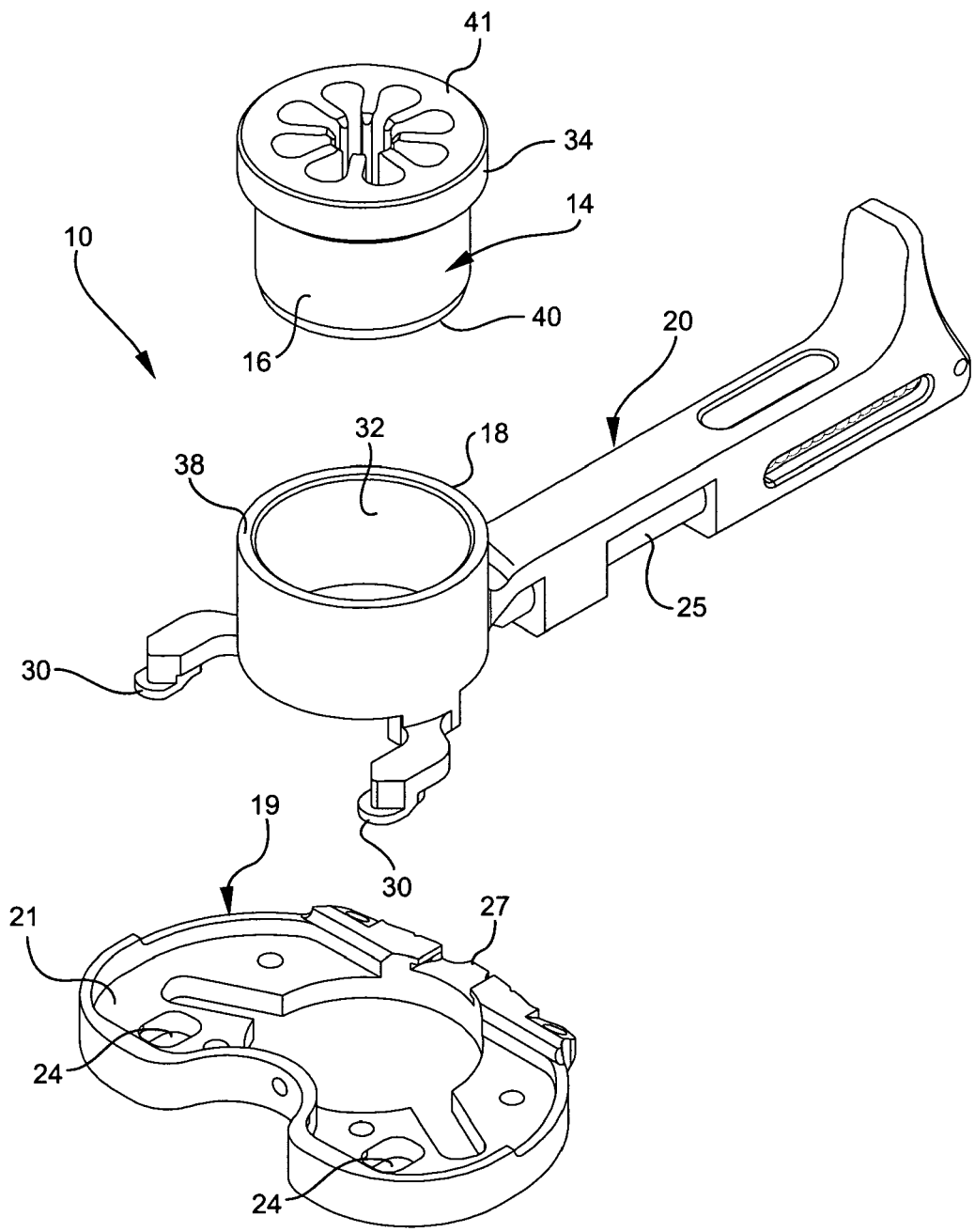
FIGS. 1 and 2 are exploded isometric views of a tibia reaming system of the present invention including a trial tibial baseplate.
Figure 2:
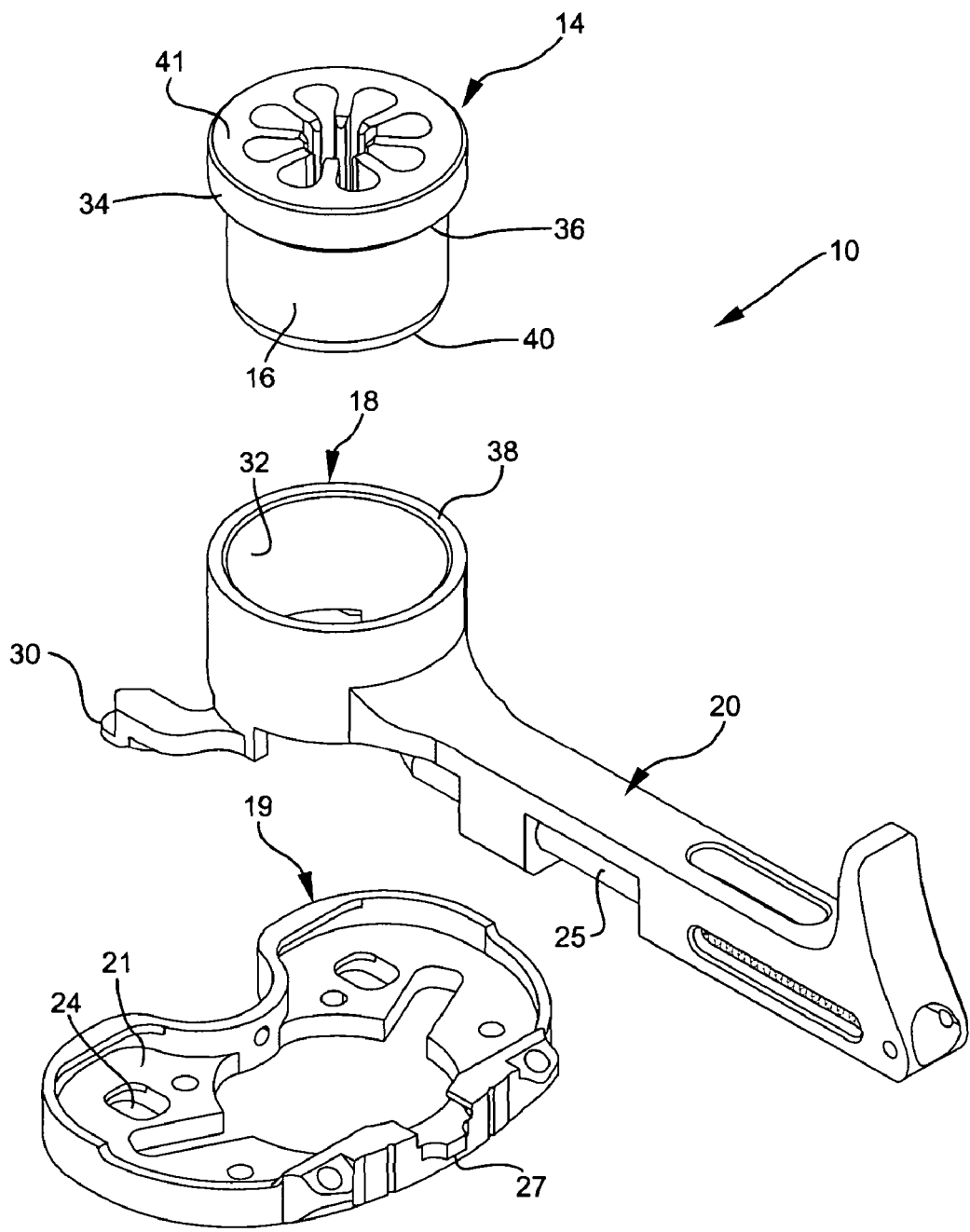
Figure 3:
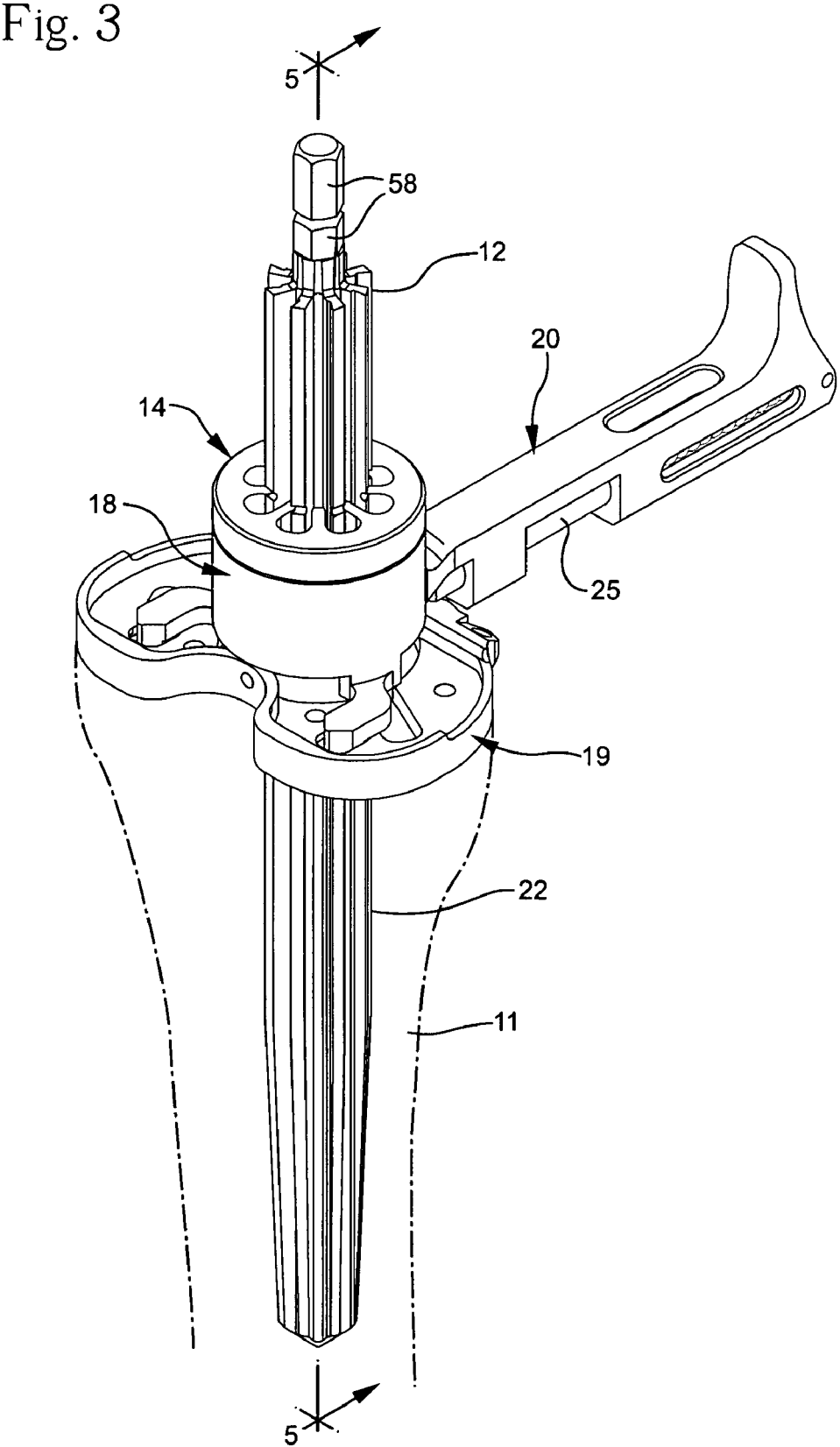
FIGS. 3 and 4 are isometric views of the assembled holder/bushing of the system shown in FIGS. 1 and 2.
Figure 4:
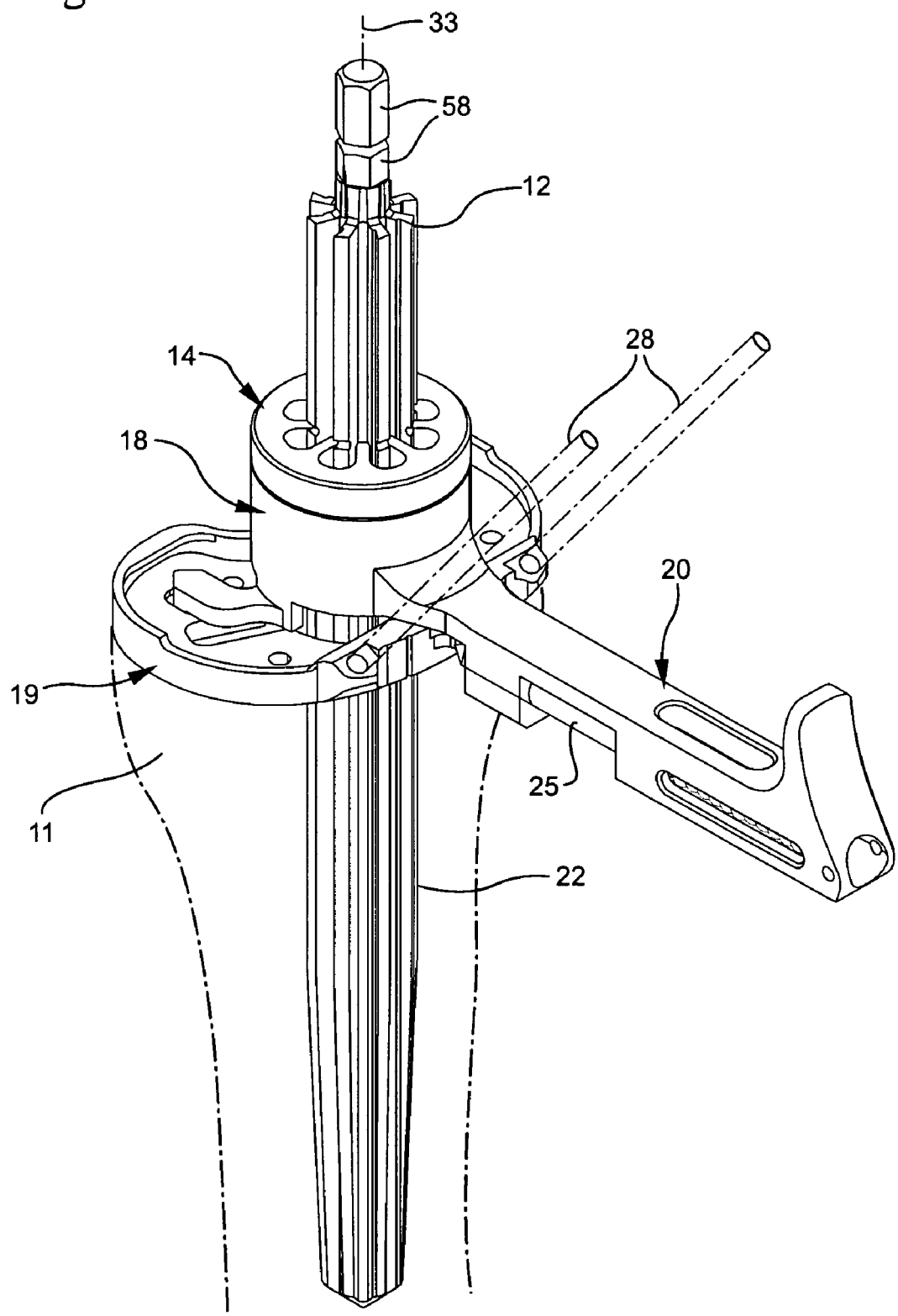

Referring to FIGS. 3 and 4, there is shown system 10 assembled on the proximal surface of tibia 11. Trial baseplate 19 is pinned in place as shown in FIG. 4 so that a series of progressively diametrically larger reamers can be inserted within bushing 16 with their axes of rotation 33 being accurately coaxially aligned. Progressive reaming proceeds by substituting reamers of progressively larger diameters within a single bushing 14.

Referring to FIGS. 12 to 18, there is shown the preferred bushing 14 and reamers 12, 12' of the present invention. The reamer bushing is provided with recesses sized to provide clearance with the cutting teeth on the reamer. Preferably, wire EDM of clover leaf shape is preferred but could be any shape which would allow clearance could be used. Bushing 14 includes a central bore 60 having a diameter "A" formed by the tips 44 of a series of flutes 45. In the preferred embodiment, the diameter "A'" of shaft 48 of each reamer 12, 12' is slightly less than or equal to diameter "A" of bore 60. The flutes 45 forming central bore 60 define a plurality of recesses 64 extending radially from bore 60 and open to the ends 40, 41 of the bushing. In the preferred embodiment, there are eight flutes 45 and recesses 64, spaced at 45° angles around bore 60, each having an entrance 66 between adjacent flutes 45 with a width "C" sized to receive flutes 49 of reamers 12, 12'. Referring to FIG. 13, flutes 49 have a predetermined width or thickness at area 50 at the radially outer tip of flutes 49 thereof and at area 52 adjacent inner shaft 48. Area 52 is adapted to fit within recess 64 through the entrance portion 66 width "C." Bushing recesses 64 extend radially outwardly within bushing 14 to a diameter "D" which is greater than the diameter "B" of the largest reamer 12.

Figure 5:
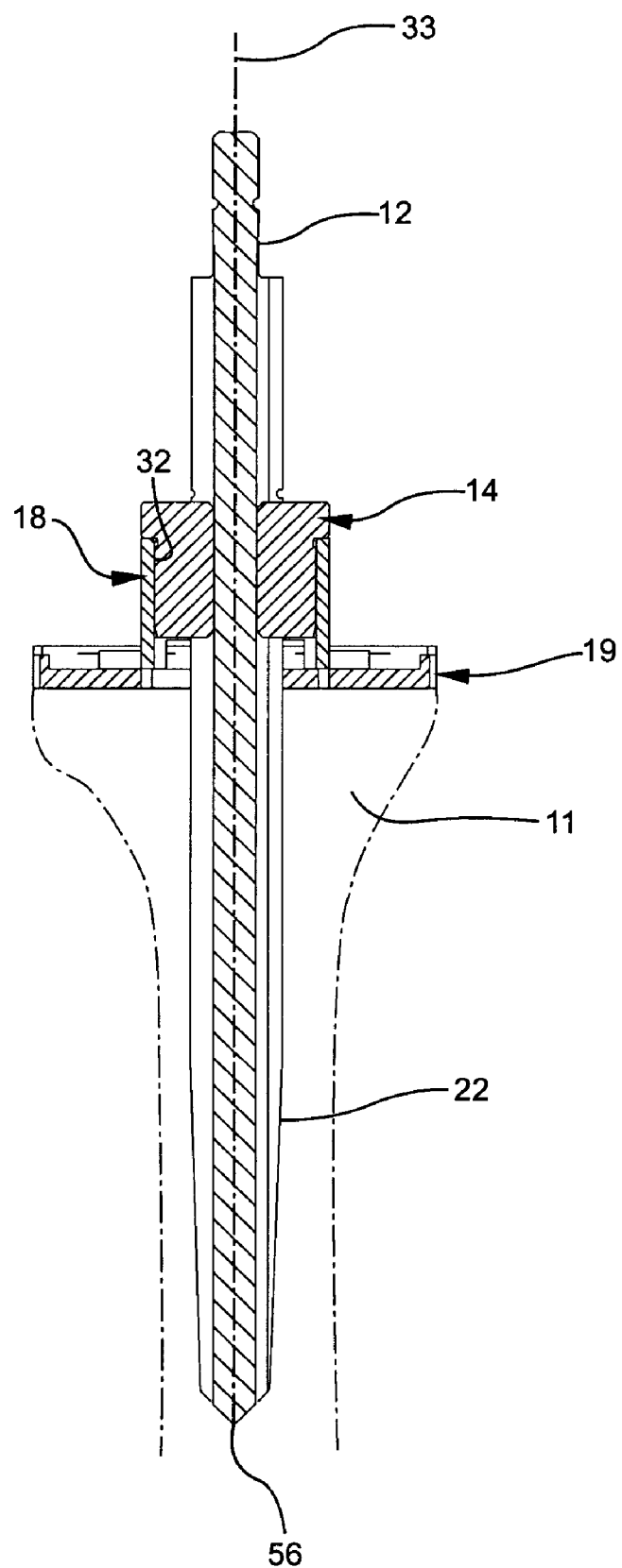
FIG. 5 is a cross-sectional view of the assembly of FIG. 3 along lines 5-5.
Figure 6:
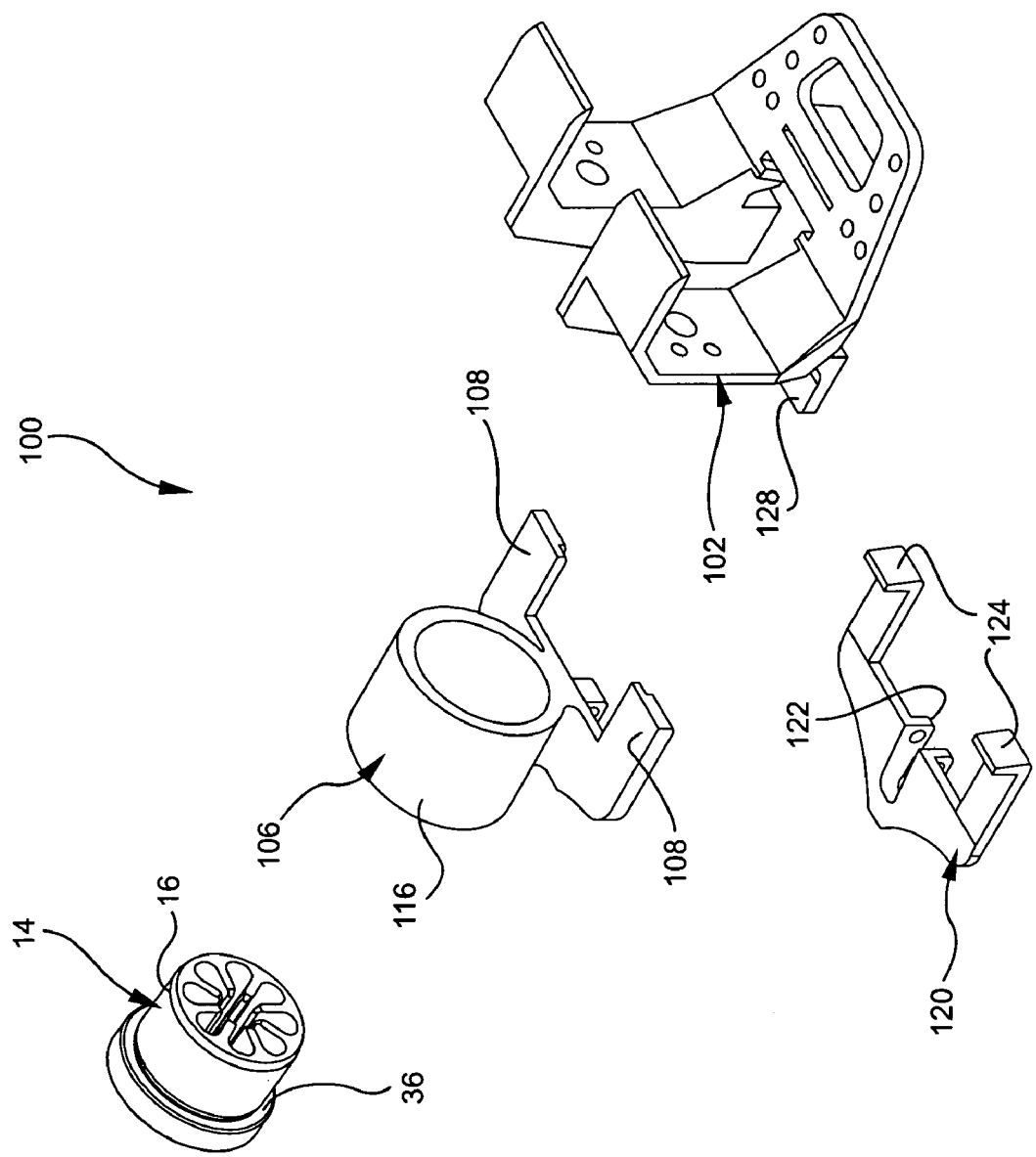
FIGS. 6 and 7 are exploded views of a femoral reaming system of the present invention, including a femoral trial.

Referring to FIG. 5, there is shown a cross-section of the reaming assembly 10 shown in FIGS. 3 and 4 mounted on tibia 11. It is appreciated that the section is taken through the dividing flute portions 45 of the bushing 14 which contact central shaft 48 of reamer 12. This area of contact serves to maintain axes 33 in the correct alignment with respect to fixture or tray 19 and bore 22.

Referring to FIGS. 6 through 11, there is shown a femoral reaming system or kit generally denoted as 100 mounted on a femur 13. Kit 100 is similar in many respects to tibial reaming system 10. Because of the similarities, similar elements are identified by the same numerals as used in describing tibial system 10. System 100 includes a femoral trial component or fixture 102 which is mounted on a distal resected femur such as by pinning with pins 104.

In the preferred embodiment, a bushing holder 106 is provided to receive bushing 14. Holder 106 is similar to holder 18 with the exception of its structure for engaging and mounting on fixture 102. Bushing holder 106 includes a pair of arms 108 which slidingly engage a pair of grooved receptacles 110 on fixture 102. In the preferred embodiment, bushing holder 106 includes a generally cylindrical inner bearing surface 112 which, in all respects, is similar to inner cylindrical bearing surface 32 of bushing 18.

Figure 7:
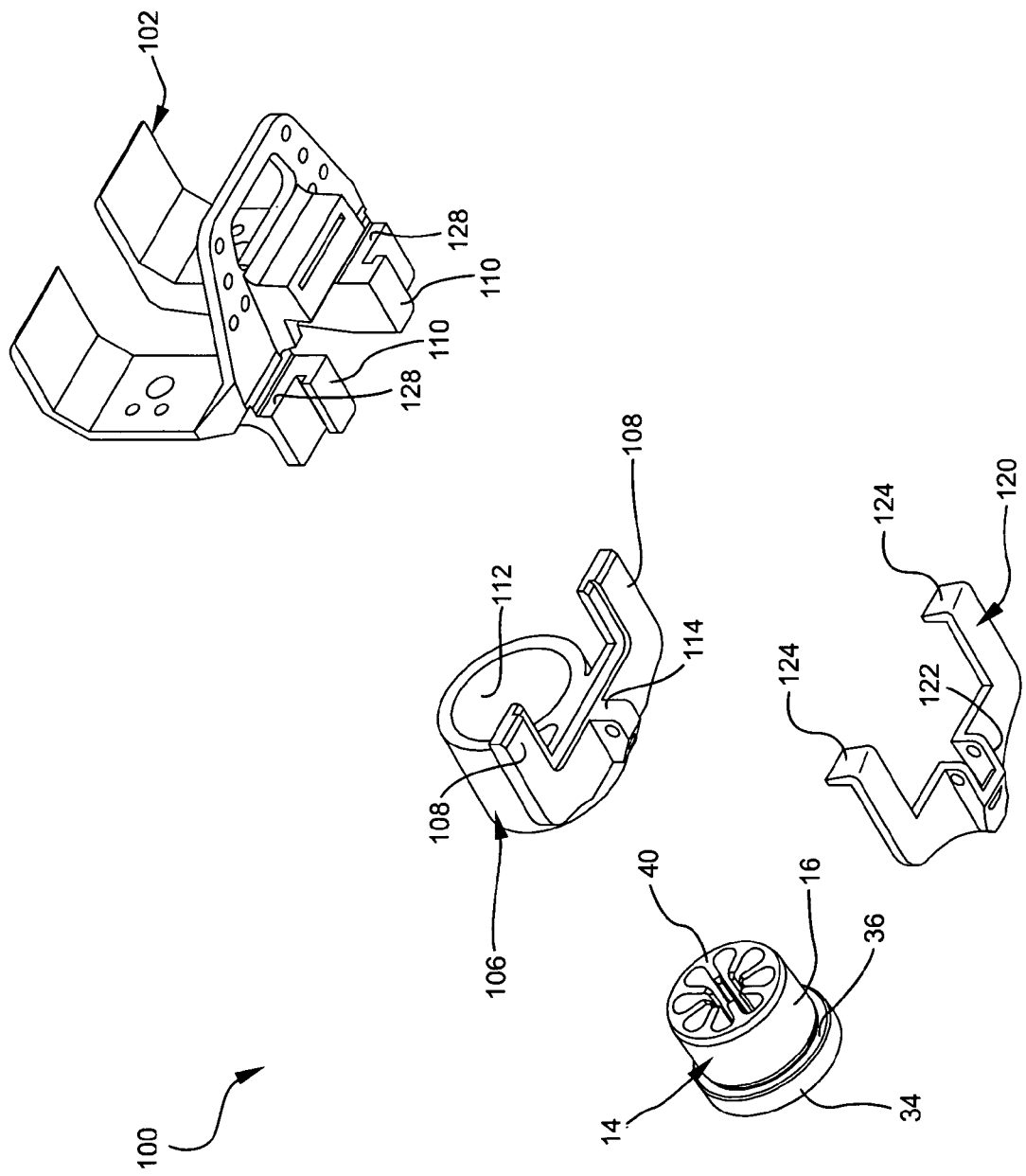

Referring to FIGS. 7 and 11, an axial locking element 120 is provided to lock bushing holder 106 on fixture 102 by preventing arms 108 disengaging from receptacles 110. Preferably, element 120 is preassembled via a pin 121 and spring connection 127 which bias element 120 to the locked position. The surgeon during use releases the lock via pressure on depression 123. Locking element 120 is attached to bushing holder 106 after its assembly on fixture 102 by a pin connection through element 114 on bushing holder 106 and flanges 122 on lock 120. While in the preferred embodiment 120 is provided, any means could be used to lock bushing holder 106 in position on fixture 102 adjacent the bone canal 22 of the femur. Locking element 120 includes a pair of flanges 124 which are adapted to engage surface 128 on the fixture 102 to prevent the axial movement of bushing holder 106 after assembly.

A bushing 14 is provided which is, in all respects, identical to bushing 14 used in the tibial system. Likewise, a series of reamers 12 may be provided which are structurally identical to those used in the tibial reaming systems, however, they may be of different incremental diameters since, in general, the medullary canal of the femur is larger than the canal of the tibia. However, in the preferred embodiment, a single set of reamers is provided for use in the tibia and femur. Thus, bushing includes surface 16 which engages surface 112 of the bushing holder 106 and flange 34 and surfaces 36 and 40. Surface 36 engages the outer surface 116 of the bushing which is identical to surface 38 of bushing 18.

Figure 8:
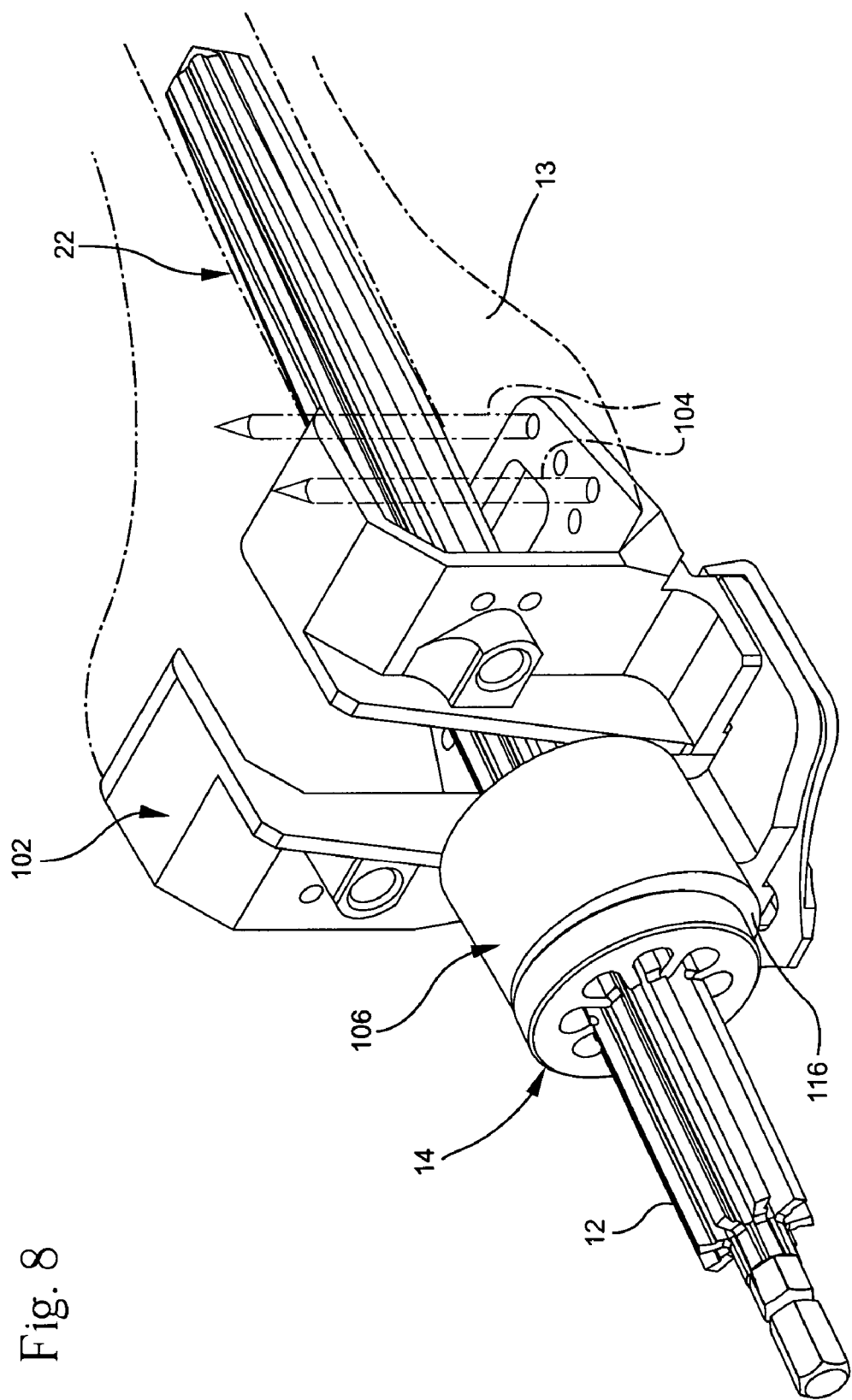
FIGS. 8 and 9 are isometric views of the assembled femoral reamer shown in FIGS. 6 and 7.
Figure 9:
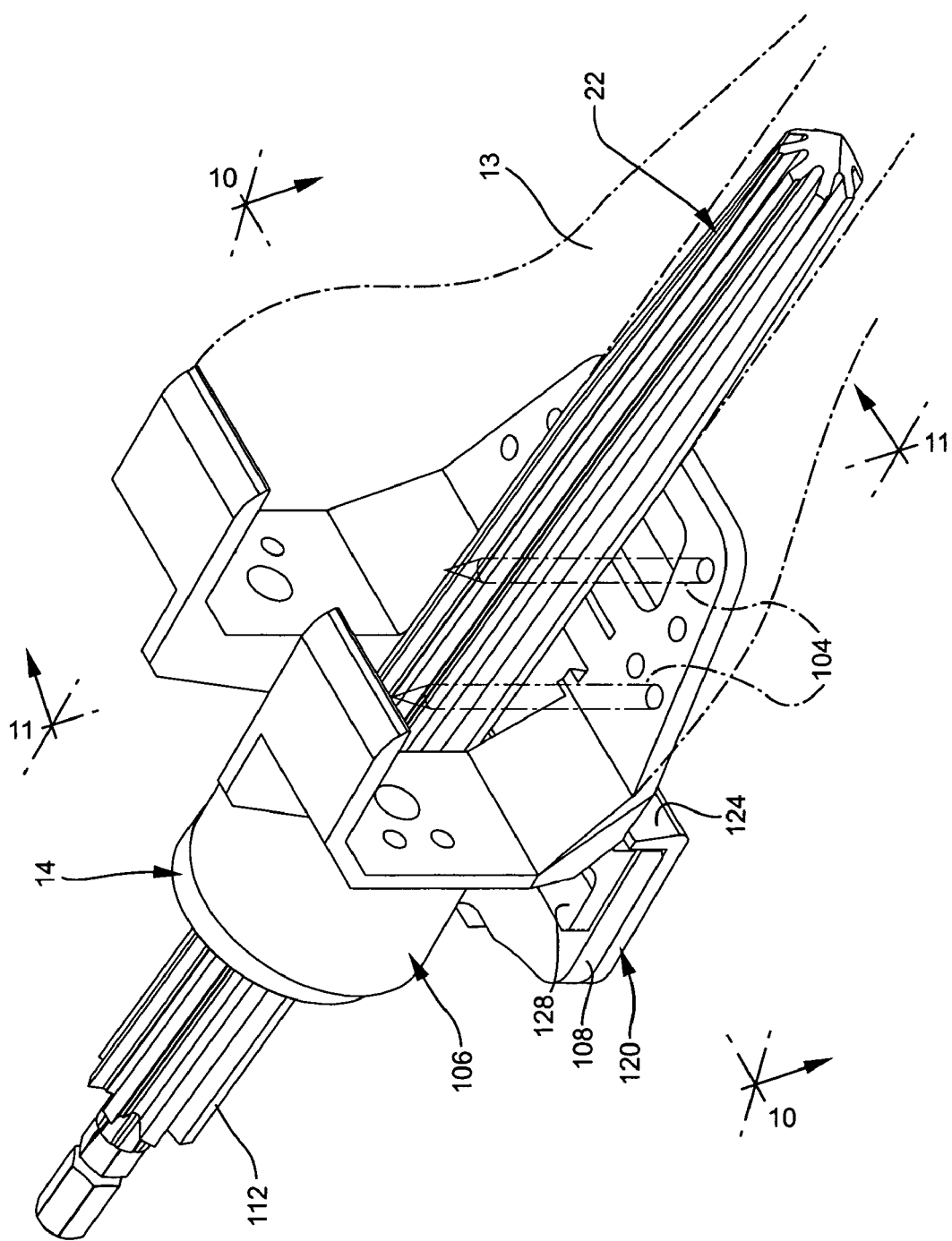

Referring to FIGS. 8 and 9, there is shown the femoral reaming system assembled to the distal end of femur 13 including bushing 14 mounted thereon receiving a reamer 12.

Figure 10:
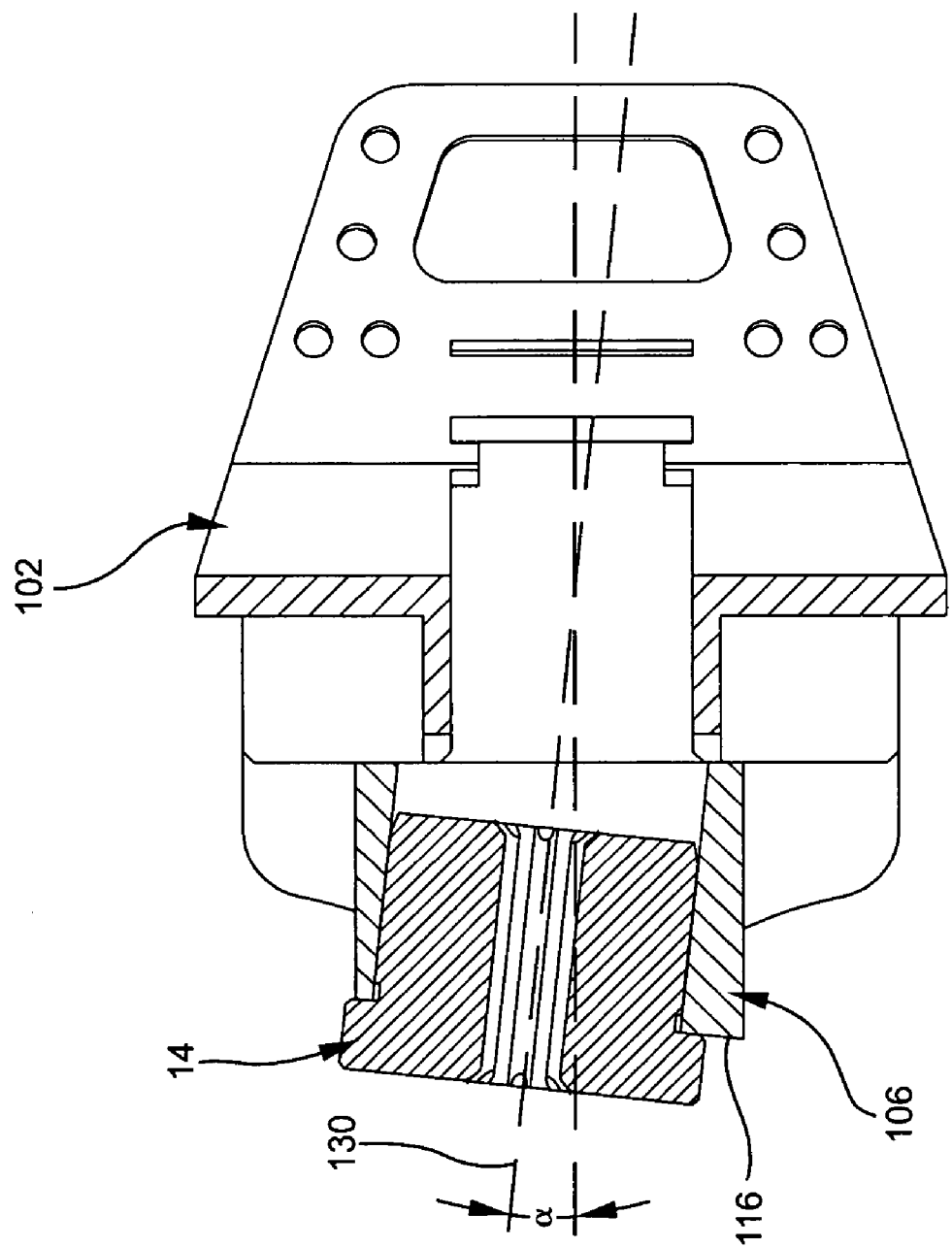
FIG. 10 is a cross-sectional view along lines 10-10 of FIG. 9.

Referring to FIGS. 10 and 11, there is shown a cross-sectional view along lines 10-10 and 11-11, respectively, of FIG. 9. It should be noted that the rotational axis 130 of bushing 14 is mounted at an angle α with respect to the surface of the distal end of femur 13 to accommodate the varus-valgus angulation of the bore 22 with respect to the distal end of the femur. Thus, the inner surface 112 of bushing 106 is angled to provide correct varus-valgus alignment. The axis 33 of reamer 12, being coaxial with axis 130 of bushing 14 will then be properly aligned. Should different angles be required, different bushings can be supplied with varying angles α.

Referring to FIGS. 12, 13 and 14, the preferred reamers 12, 12' are shown having a shaft 48 with eight straight flutes 49. In the preferred embodiment, flutes 49 extend radially outwardly from an inner shaft 48 with a diameter "B" with their radially outward portions 50 being larger in width than the areas 52 adjacent inner shaft 48. Flutes 49 extend parallel to longitudinal axis 33 of shaft 48. In the preferred embodiment, the maximum diameter "A" of inner shaft 48 of each reamer 12 is about 8 mm and consequently, the diameter "A" of bushing 16 would also be about 8 mm. In the preferred embodiment, recesses 64 of bushing 16 have a clover leaf shape with wider radially outer portions 68. Wider portions 68 are adapted to receive the portions 50 of flutes 49. Area 50 of flutes 49 may be wider than area 52 adjacent shaft 48. Thus, the dimension "C" of recess 64 is generally equal to the width of flute 49 in the area 52 adjacent the outer diameter of inner shaft 48 but may be less than the width at area 50. The variable outer diameter "B" of reamers 12 is always less than the maximum diameter "D" of bushing 14. Reamers are well known in the orthopedic art and any reamer design having straight flutes can be used with the bushing 14 of the present invention.

As shown in FIGS. 12 and 14, the leading end 54 of reamers 12, 12' is inwardly conically tapered toward tip 56 to allow for its ease of introduction into bone bore 22. In addition, the drive end 57 of reamers 12, 12' includes a drive portion 58, which in the preferred embodiment, is in the form of a hex which may be placed into the chuck of any convenient rotary power instrument such as an electric or pneumatic drill (not shown).

Since the use of tibial reaming system 10 and femoral reaming system 100 is similar only use of the tibial system 10 will be described. During use of tibial system 10, bushing holder 18 is affixed in any convenient manner with respect to a bone bore 22 such as by using mounting plate 19. Bushing 14 is then placed within bushing holder 18 and then the smallest diameter reamer of the reamers 12, 12' in the kit is placed through the bore 60 and recesses 64 of bushing 14. The reamer is then rotated by a power source, which rotation in turn rotates surfaces 16 and 36 of bushing 14 against surfaces 32 and 38 of holder 18. The reamer may have to be advanced downwardly within the bore 22. Once the reamer has reamed the tibial bore 22 to the appropriate depth, it is withdrawn and the next incrementally larger sized reamer 12' is mounted on the rotary drive source and inserted within the same bushing 14. This second reamer 12' incrementally increases the diameter of bore 22. Any number of incrementally larger reamers may be used to increase the diameter of bore 22 to its desired final diameter.

In the preferred embodiment, sixteen (16) reamers from 8-23 mm in one millimeter increments of increasing diameters are supplied in a kit form, along with at least one rotary bushing and a series of bushing holders adapted to be mounted on various trial instruments or other fixtures adapted to be fastened to a bone or any desired work piece. If a large number of reamers need to be used, it may be necessary to vary the inner shaft diameter 48 of reamers 12 and thus provide additional bushings 14 having matching bores 60.

Once the final diameter of bore 22 has been reached, then the assembly of bushing 16, bushing holder 18 and mounting plate 19 is removed from the work piece or bone. In the preferred embodiment, reamers range from 8 mm to 23 mm in 1 mm increments. However, a larger number of reamers could be provided varying in size of only 0.5 mm. Thus, thirty-one (31) reamers could be provided for enlarging bores from 8 mm to 23 mm at 0.5 mm increments.

While only the use of the reamer instrument kit for the tibia have been described in detail use of the femoral reamer kit to progressively enlarge the intramedullary canal of the femur would be identical. Furthermore, use of similar progressive reaming kits for enlarging other bone canals such as the humeral canal are well within the scope of the invention. Furthermore, the system could be used to progressively enlarge bores such as in plastic or fiberglass which may crack if a large hole is drilled in one step.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A reamer bushing mounted in a fixture adapted for being aligned with a bone canal, the bushing for use with at least two different diameter rotatable bone reamers, the reamers each having a plurality of longitudinal flutes extending from an inner shaft, outer radial ends of the flutes defining the reamer diameter, the bushing comprising:
   a body with an outer bearing surface for rotatably engaging a surface of the fixture in which the bushing is mounted;
   a longitudinal bore formed in the body for receiving the inner shaft of the reamer; and
   a plurality of recesses extending radially outward of said bore and open thereto, each recess for receiving at least one of said plurality of flutes of said bone reamers.

2. The reamer bushing as set forth in claim 1 wherein said recesses extend radially from said bushing body longitudinal bore a distance greater than a largest radial extent of the flutes of the at least two reamers.

3. The reamer bushing as set forth in claim 2 wherein the bushing has a number of recesses equal to or greater than the plurality of flutes on each of said reamers.

4. The reamer bushing as set forth in claim 1 wherein said recesses expand in width on moving radially outwardly from said bushing body longitudinal bore.

5. The reamer bushing as set forth in claim 4 wherein said reamer flutes expand in width in moving radially outwardly from said inner shaft.

6. The reamer bushing as set forth in claim 1 wherein said bushing has at least three recesses formed therein.

7. The reamer bushing as set forth in claim 1 wherein said recesses each receive at least two flutes.

8. The reamer bushing as set forth in claim 1 wherein the bushing body is cylindrical and said outer bearing surface extends circumferentially around an outer cylindrical surface of the bushing.

9. The reamer bushing as set forth in claim 8 wherein said cylindrical outer bearing surface extends about an axis which is coaxial with an axis of said longitudinal bore.

10. The reamer bushing as set forth in claim 9 wherein said plurality of recesses have radial ends opposite ends thereof open to said bore at a shorter radial distance from said axis of said longitudinal bore than said outer cylindrical surface of the bushing.

11. The reamer bushing as set forth in claim 10 wherein said recesses expand in width on moving radially outwardly from said bushing body longitudinal bore.

* * * * *

UNITED STATES PATENT AND TRADEMARK OFFICE
CERTIFICATE OF CORRECTION

PATENT NO.       : 7,867,234 B2
APPLICATION NO.  : 10/679569
DATED            : January 11, 2011
INVENTOR(S)      : Carlos E. Collazo It is certified that error appears in the above-identified patent and that said Letters Patent is hereby corrected as shown below:

Title page, Item (57) Abstract, line 3, "different reamers" should read --different diameters--.
Column 1, line 18, "using a smallest" should read --using the smallest--.
Column 1, line 42, "reamer extend" should read --reamer extending--.
Column 1, line 43, "from a smallest" should read --from the smallest--.
Column 2, line 25, "conforms" should read --conform--.
Column 2, line 50, "well know in the art" should read --well known in the art--.
Column 4, line 4, "there is shown" should read --there are shown--.
Column 4, line 61, "embodiment 120" should read --embodiment lock 120--.
Column 5, line 9, "bushing includes" should read --bushing 14 includes--.
Column 5, line 38, "clover leaf" should read --cloverleaf--.
Column 6, line 28, "have been described" should read --has been described--.

Signed and Sealed this
Twentieth Day of March, 2012

David J. Kappos
*Director of the United States Patent and Trademark Office*